(12) United States Patent
Mazzeo (10) Patent No.: US 11,850,722 B2
(45) Date of Patent: Dec. 26, 2023

(54) MEDICAL INSTRUMENT

(71) Applicant: Storz am Mark GmbH, Emmingen-Liptingen (DE)

(72) Inventor: Martin Mazzeo, Emmingen Liptingen (DE)

(73) Assignee: Storz am Mark GmbH, Emmingen-Liptingen (DE)

( * ) Notice: Subject to any disclaimer, the term of this patent is extended or adjusted under 35 U.S.C. 154(b) by 0 days.

(21) Appl. No.: 17/057,449

(22) PCT Filed: May 21, 2019

(86) PCT No.: PCT/EP2019/063090
§ 371 (c)(1),
(2) Date: Nov. 20, 2020

(87) PCT Pub. No.: WO2019/224196
PCT Pub. Date: Nov. 28, 2019

(65) Prior Publication Data
US 2021/0213599 A1    Jul. 15, 2021

(30) Foreign Application Priority Data
Mar. 23, 2018  (DE) ..................... 10 2018 112 346.9

(51) Int. Cl.
*A61B 17/062* (2006.01)
*A61B 17/30* (2006.01)
(Continued)

(52) U.S. Cl.
CPC ............ *B25G 1/102* (2013.01); *A61B 17/062* (2013.01); *A61B 17/30* (2013.01);
(Continued)

(58) Field of Classification Search
CPC ... A61B 17/30; A61B 17/3201; A61B 17/062; A61B 2017/305; A61B 2017/0042;
(Continued)

(56) References Cited

U.S. PATENT DOCUMENTS 419,851 A  1/1890  Grisel
419,852 A  1/1890  Hambay
(Continued)

FOREIGN PATENT DOCUMENTS

DE  102007047059 A1  4/2009
DE  202010008512 U1  11/2010
(Continued)

OTHER PUBLICATIONS

International Search Report (with translation) dated Jul. 17, 2019, relating to International Application No. PCT/EP2019/063090.
(Continued)

*Primary Examiner* — Kelly J Bekker
*Assistant Examiner* — Mohammed S Adam
(74) *Attorney, Agent, or Firm* — Bodman PLC (57) ABSTRACT

A medical instrument is provided with a first arm extending in a longitudinal direction and having a grip area between a rear end and a front working end. At least two elongated holes are formed in the grip area, which are arranged offset to each other in the longitudinal direction.

16 Claims, 6 Drawing Sheets

(51) Int. Cl.
*A61B 17/3201* (2006.01)
*A61B 17/00* (2006.01)
*B25G 1/10* (2006.01)
*A61C 3/10* (2006.01)

(52) U.S. Cl.
CPC .. *A61B 17/3201* (2013.01); *A61B 2017/0042* (2013.01); *A61C 3/10* (2013.01)

(58) Field of Classification Search
CPC ............ A61B 2017/2936; A61B 10/06; A61B 2018/1462; A61B 17/32053; A61B 2017/00429; A61B 2017/00433; A61B 17/28; A61B 17/00; B25G 1/102; A61C 3/10; A61C 3/00
See application file for complete search history.

(56) References Cited

U.S. PATENT DOCUMENTS

| | | |
|---|---|---|
| 433,914 A | 8/1890 | Stokes |
| 938,187 A | 10/1909 | Walker |
| 3,738,366 A * | 6/1973 | Blomberg .............. A61B 17/30 294/99.2 |
| 4,225,667 A | 9/1980 | Ruben |
| 4,527,331 A | 7/1985 | Lasner et al. |
| 5,019,091 A * | 5/1991 | Porat ...................... A61B 17/30 606/205 |
| 2002/0077649 A1* | 6/2002 | Lasner ............... A61B 17/2841 606/174 |
| 2007/0265546 A1* | 11/2007 | Porat ...................... A61B 10/06 600/564 |
| 2010/0298865 A1* | 11/2010 | Aufaure ................ A61B 17/30 606/210 |
| 2013/0247333 A1 | 9/2013 | Bender et al. |
| 2014/0005661 A1 | 1/2014 | Shelton, IV et al. |
| 2016/0361079 A1* | 12/2016 | Storz ...................... A61B 17/28 |
| 2017/0224399 A1 | 8/2017 | Coillard-Lavirotte et al. |
| 2017/0360465 A1* | 12/2017 | Smith ................ A61B 17/3201 |

FOREIGN PATENT DOCUMENTS

| | | |
|---|---|---|
| EP | 0181976 * | 5/1986 |
| EP | 2281516 A1 | 2/2011 |
| WO | WO-2012/109594 A2 | 8/2012 |
| WO | WO-2012/161782 A1 | 11/2012 |
| WO | WO-2015/100325 A1 | 7/2015 |

OTHER PUBLICATIONS

International Preliminary Report on Patentability dated Sep. 9, 2020, relating to International Application No. PCT/EP2019/063090.

* cited by examiner

MEDICAL INSTRUMENT

CROSS-REFERENCE TO RELATED APPLICATIONS

This application is a National Phase Application of International Application PCT/EP2019/063090, filed May 21, 2019, which claims priority to German Patent Application No. DE 10 2018 112 346.9, filed May 23, 2018, the disclosures of which are incorporated herein by reference in their entirety.

TECHNICAL FIELD

The present disclosure relates to a medical instrument (in particular a dental instrument) having a first arm extending in a longitudinal direction and having a grip area between a rear end and a front working end.

BACKGROUND

With such instruments, it is important that a user can hold the medical instrument well and safely, i.e. without slipping.

SUMMARY

It is therefore a purpose of the invention to provide a medical instrument (in particular a dental instrument) with a first arm extending in a longitudinal direction and having a grip area between a rear end and a front working end, which can be held securely by a user.

The medical instrument (in particular a dental instrument) according to an aspect of the invention has a first arm extending in a longitudinal direction and comprises a grip area between a rear end and a front working end, wherein at least two elongated holes extending in a longitudinal direction are formed in the grip region, which are arranged offset to each other in the longitudinal direction. Advantageously, the elongated holes are designed in such a way as to give a user a grip to prevent slipping.

By providing the elongated holes, the weight of the medical instrument can be reduced in an advantageous way. The handling of the medical instrument is also improved.

For example, elongated holes provide an advantageous way of ensuring that a user slips significantly less with his fingers, with which he holds the grip area, compared to known medical instruments which do not have the arrangement of elongated holes according to an aspect of the invention. Furthermore, reprocessing of the medical instrument according to an aspect of the invention is well possible.

In particular, the ends (hereafter also referred to as longitudinal ends) of the elongated holes, which delimit the elongated holes in the longitudinal direction, can provide the user with a grip to prevent slipping, so that due to the minimum of two elongated holes, different favourable grip positions are provided where slipping is prevented.

Due to the elongated holes there is therefore an improved haptic, which is helpful for example with rotary movements, pulling movements, pushing movements and/or pressure movements of the medical instrument. The offset arrangement of the at least two elongated holes in the longitudinal direction means in particular that at least the front or rear longitudinal ends of two elongated holes are offset to each other in the longitudinal direction and are therefore not at the same level.

In the case of the medical instrument according to an aspect of the invention, the at least two elongated holes can extend in the longitudinal direction. In some examples, they extend parallel to the longitudinal direction. However, one or more or all of the elongated holes can also enclose an angle with the longitudinal direction which is greater than 0° and less than or equal to 90°.

It is also possible that at least two elongated holes cross or intersect.

At least two of the elongated holes can be spaced from each other in the longitudinal direction. In other words, the elongated holes can be arranged one behind the other in the longitudinal direction.

In addition, at least two of the elongated holes can lie on a straight line, where in some implementations the straight line extends parallel to the longitudinal direction. Alternatively or additionally, the at least two elongated holes can be arranged offset to each other transversely to the longitudinal direction.

At least one of the elongated holes can be designed as a through hole or as a groove.

Furthermore, at least one of the longitudinal ends of the elongated holes can be rounded. The at least two elongated holes can have the same dimensions or differ in length and/or width. Alternatively, the longitudinal ends can also be square or triangular.

The grip area can have two or three or more groups of at least two elongated holes (in particular two or three), each offset from the other in the longitudinal direction. The groups of elongated holes can be offset to each other transversely to the longitudinal direction.

The groups of at least two elongated holes can run parallel to each other. However, it is also possible that the groups of at least two elongated holes enclose an angle with each other and therefore do not run parallel to each other. The angle can preferably be in the range of greater than 0° and less than or equal to 20° and in particular less than or equal to 15° or 10°.

Furthermore, at least one of the elongated holes can have two sides running parallel to each other.

In addition, several grooves can be formed in the grip area, spaced apart from one another in the longitudinal direction, which run transverse to the longitudinal direction, so that a raised or protruding area is present between two adjacent grooves. This further improves the feel of the grip area.

Alternatively, the grip area can be designed so that it has a smooth surface except for the elongated holes. The grip area can be either flat or curved or bent.

The grip area can be curved in the area of the elongated holes, which may be cut transverse to the longitudinal direction. This can reduce the weight of the medical instrument, as the arch shape provides the required strength or stiffness of the medical instrument and thus the material thickness can be reduced.

The medical instrument can have exactly the first arm and therefore a single arm. In this case, it can be called a one-armed instrument, for example, wherein it has the front working end and therefore is single-ended. However, it is also possible that the rear end is also a working end, so that the medical instrument can then be described as having two ends.

The medical instrument may also be designed as a two-armed instrument, in which case it comprises a second arm extending in the longitudinal direction and having a grip area between a rear end and a front working end. The two arms are connected to each other at their rear ends and/or at their front working ends. Preferably, the two arms can be moved towards each other (i.e. pressed together) by a user, for example when the user presses the two grip areas with thumb and index finger. Such a two-armed medical instrument can be, for example, pliers, dental pliers, a needle holder, scissors or tweezers.

Such a two-armed medical instrument may have at least two elongated holes extending in longitudinal direction in the grip area of the second arm, which are arranged offset to each other in the longitudinal direction. This considerably reduces the possibility of the user slipping.

The grip area of the second arm can be embodied in the same way as the grip area of the first arm. The two gripping areas can be the same or different.

It goes without saying that the features mentioned above and those to be explained below can be used not only in the combinations indicated but also in other combinations or on their own without leaving the scope of the present invention.

In the following, the invention is explained in more detail by means of embodiments with reference to the attached drawings, which also disclose inventive features. These examples are for illustrative purposes only and should not be interpreted as restrictive. For example, a description of an embodiment comprising a large number of elements or components is not to be interpreted as meaning that all these elements or components are necessary for implementation. Rather, other embodiments may contain alternative elements and components, fewer elements or components, or additional elements or components. Elements or components of different embodiments may be combined unless otherwise specified. Modifications and variations described for one of the examples may also be applicable to other examples. In order to avoid repetition, identical or corresponding elements in different figures are marked with the same reference signs and not explained more than once.

DETAILED DESCRIPTION

Figure 1:
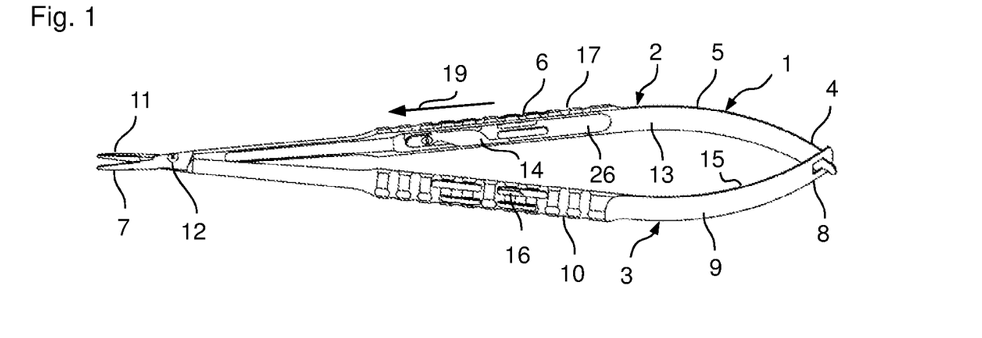
FIG. 1 is a perspective view of a first embodiment of a medical instrument according to the invention.

In the embodiment shown in FIG. 1, the medical instrument 1, which can therefore be described in particular as a dental instrument, needle holder, pliers, medical clamp, scissors, or tweezers, comprises a first arm 2 and a second arm 3.

The first arm 2 comprises a first rear end 4, followed by a first transition area 5, followed by a first grip area 6. From the first grip area 6 the first arm 2, which can also be called the first leg 2, extends to its first front working end 7, which here is designed as the first grip jaw 7.

Similarly, the second arm 3 has a second rear end 8, from which a second transition area 9 extends to a second grip area 10. The second grip area 10 then merges into the second front working end 11, which here is designed as a second grip jaw 11.

The first rear end 4 and the second rear end 5 are designed so that one of the two ends protrudes through a through hole formed in the other of the two ends. To prevent one end from slipping out of the other end, a thickening is provided at the outermost end of the end that protrudes through the through hole. In other words, the first rear end 4 and the second rear end 5 are plugged into each other and are thus movably connected.

In order to provide the functionality of the medical instrument 1, the two arms 2 and 3 cross in front of the front working ends 7, 11, wherein the arms are connected to each other in the crossing area via a swivel joint 12. In the basic position shown in FIG. 1, the two working ends 7, 11 are in the open position, so that there is a jaw-like grip structure. If the two arms 2, 3, the rear ends 4, 8 of which are connected to each other as described above, are pressed together by a user, which is possible because the transition areas 5, 9 are elastic, the distance between the two arms 2, 3 is reduced, thus closing the jaw-like opening of the grip jaws 7, 11. An object previously positioned between the grip jaws 7, 11, such as a needle, is thereby clamped by the grip jaws 7, 11. In this position an object can therefore be held between the grip jaws 7, 11, which is why this position is called a holding position. The instrument 1 can therefore be described in particular as a needle holder. It can generally be described as medical pliers, a medical clamp or a medical holding element. If the user stops pressing the two arms 2, 3 together, the medical instrument 1 will return to the basic position shown in FIG. 1. In other words, the elastically designed transition areas 5, 9 in particular cause a restoring force to act, which returns the medical instrument 1 to the basic position in which the grip jaws 7, 11 are open.

Figure 2:
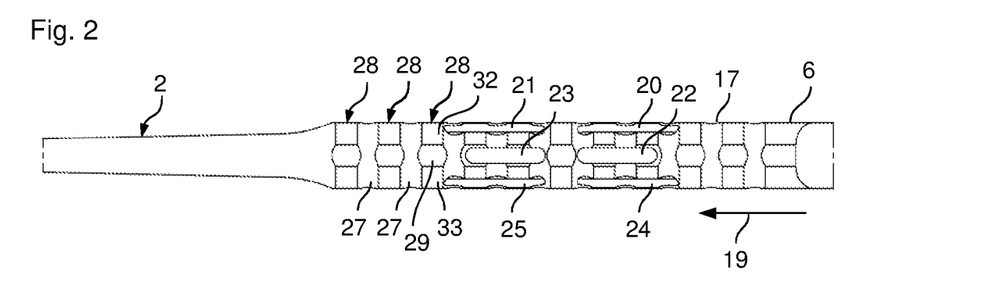
FIG. 2 is an enlarged top view of a grip area of a first arm of the instrument of FIG. 1.
Figure 3:
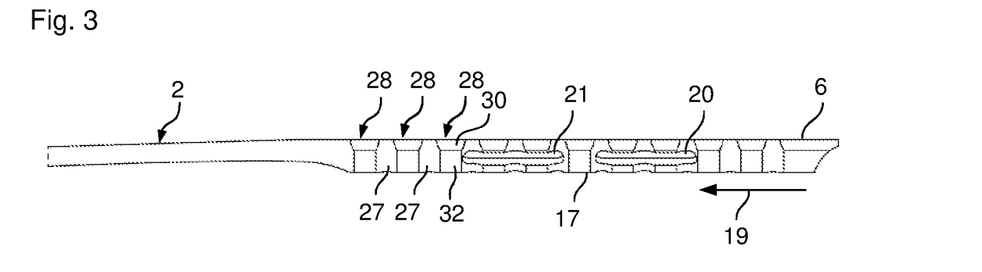
FIG. 3 is an enlarged side view of the grip area of the first arm of the instrument of FIG. 1.
Figure 4:
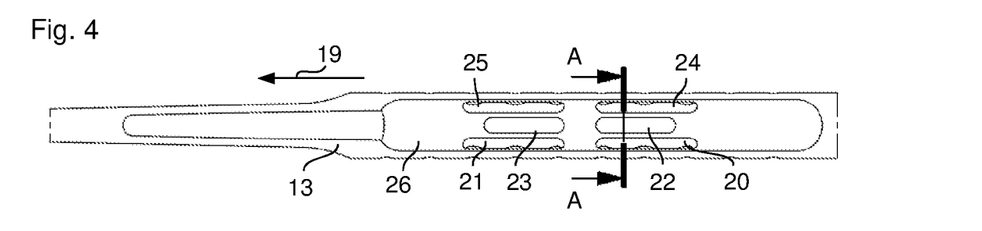
FIG. 4 is an enlarged rear view of the grip area of the first arm of the instrument of FIG. 1.
Figure 5:
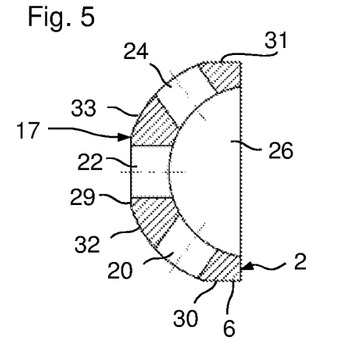
FIG. 5 is a sectional view of the grip area of the first arm of the instrument according to the cutting line A-A in FIG. 4.

FIGS. 2 to 4 show enlarged representations of the first grip area 6 of the first arm 2, in order to be able to explain the design of the first grip area 6 in more detail. In FIG. 5, section A-A is shown according to the line of intersection in FIG. 4.

As can be seen in FIG. 1, a first locking element 14 is attached to the inner side 13 of the first arm 2, which protrudes from the inner side 13 towards the second arm 3. On the inner side 15 of the second arm 3 a second locking element 16 is attached, which is corresponding or complementary to the first locking element 14 and is partially visible through an elongated hole in the second grip area as shown in FIG. 1. If the medical instrument 1 is in the holding position and the user presses the two arms 2, 3 further together, the second locking element 16 engages with the first locking element 14 in such a way that the holding position is fixed or held, even if the user no longer presses the two arms 2, 3 together, so that secure gripping with the two grip jaws 7 and 11 is possible. In doing so, the two grip jaws 7, 11 exert a constant, pre-adjustable holding force on the object to be held. In particular, the holding force can be adjusted by the first and second locking elements 14, 16 by defining via the first and second locking elements 14, 16 how close together the two arms 2, 3 are held in the holding position. In other words, by pressing the two arms 2, 3 together, a user can engage the first locking element 14 with the second locking element 16 in such a way that the holding position is maintained even if the user puts the medical instrument 1 down, for example. If the medical instrument 1 is in the holding position so that the two grip jaws 7, 11 are closed, the user can release the first locking element 14 from the second locking element 16 by pressing the two arms 2, 3 together again so that the medical instrument 1 is no longer held in the holding position by the locking elements. If the user then stops pressing the two arms 2, 3 together, the medical instrument 1 can return to its basic position.

However, the locking elements 14, 16 are not absolutely necessary and can also be omitted. Therefore, the first locking element 14 is not shown in the illustrations in FIGS. 2 to 5.

Since the second grip area 10 is basically designed in the same way as the first grip area 6, only the first grip area 6 is described in detail below.

Figure 6:
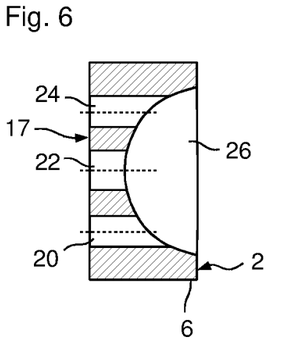
FIG. 6 is a sectional view of an additional example of a grip area that is a modification of the grip area of the first arm in the same representation as in FIG. 5.

In order to prevent the user's fingers from slipping when using the medical instrument 1, the first grip area 6 has three pairs of two elongated holes 20, 21; 22, 23; 24, 25, arranged one behind the other in the longitudinal direction 19 of the first arm 2. Each pair of elongated holes 20, 21; 22, 23; 24 and 25 is arranged in the embodiment described here in such a way that the elongated holes 20-25 of each pair lie with their longitudinal axes on a straight line parallel to the longitudinal direction 19. The elongated holes 20-25 are in particular characterized in that their extension L in the longitudinal direction (as shown in FIG. 6 for the enlarged elongated hole 22) is at least twice as large as their extension B transverse to the longitudinal direction 19. Preferably, the extension of the elongated hole in the longitudinal direction is 19 x times as large as the extension of the elongated hole transverse to the longitudinal direction 19, whereby x is in the range of 2 to 70 and preferably 2 to 10 or 5 to 8. The width B can be in the range from 1 mm to 15 mm. In particular, it can be in the range of 1 mm to 10 mm or 1.5 mm to 5 mm. It is also possible that the width is 2 mm. The length L can be in the range of 2 mm to 70 mm. A range of 2 mm to 35 mm is preferred and in particular a range of 2 mm to 26 mm. For example, the length L can be 20, 26, 35 or 70 mm.

Figure 8:
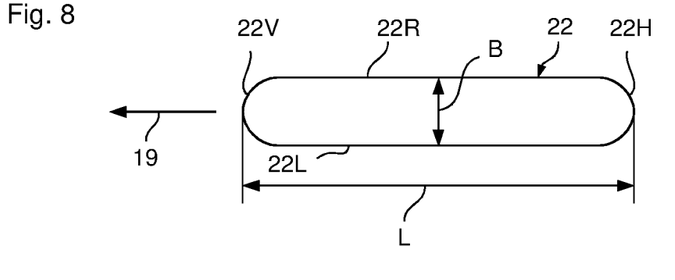
FIG. 8 is a schematic enlarged view of an elongated hole in the grip area of the first arm of the instrument of FIG. 1.
Figure 9:
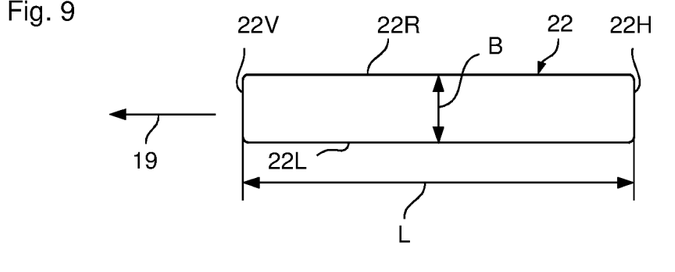
FIG. 9 is a schematic enlarged view of an additional example of an elongated hole according to a variation from that shown in FIG. 8.

Preferably, the elongated holes 20-25, as shown in FIG. 8 for the elongated hole 22, are characterized in that they have two parallel longitudinal sides 22R and 22L. The longitudinal sides 22R and 22L are connected by a rear end 22H and a front end 22V. The extension of the longitudinal sides 22R, 22L is preferably at least 50% of the extension L in the longitudinal direction 19. Preferably, the extension of the longitudinal sides 22R, 22L can be at least 60%, 70%, 80%, 90% or 95% of the extension L. It is also possible that the extension 22R, 22L is practically 100% of the extension L, as shown schematically in FIG. 9. In this case, the front and rear ends 22V and 22H are not rounded as shown in FIG. 8, but run in particular perpendicular to the direction of extension of the longitudinal sides 22R, 22L.

It can also be said that the extension B transverse to the longitudinal direction 19 and thus the width B of the elongated holes 20-25 (except possibly for the front and rear end 22V, 22H) is constant.

As can be seen in particular from the sectional view in FIG. 5, the first grip area 6 is of arcuate design and has an approximately circular ring-shaped cross-section, wherein the elongated holes 20-25 are designed as through holes 20-25 so that they extend completely through the wall in the first grip area 6. Alternatively, it is possible to form the elongated holes 20-25 in the form of grooves, in which case they are only open towards the first outer side 17 of the first arm 2. However, the design as through holes is advantageous, in particular from the point of view of cleaning, disinfection and/or sterilisation (in particular reprocessing) of the medical instrument 1.

Since the cross-sectional shape of the first grip area 6 is basically circular segmental, an inner recess 26 is formed on the first inner side 13, which again has a cross-sectional shape essentially in the shape of a circular segment, as can be seen in FIG. 5. In other words, the grip area 6 is arched so that it is bent or bulged outwards, i.e. pointing away from the second arm 3. This has the advantage of keeping the weight of the medical instrument 1 low, as the required strength or rigidity is ensured by geometrically shaping the grip area 6.

Due to the inner recess 26, the first inner side 13 of the first arm 2 is continuously curved in the area of the first grip area 6. The continuous curvature is only interrupted by the elongated holes 20 to 25.

Figure 7:
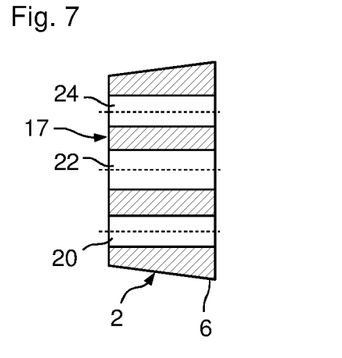
FIG. 7 is a sectional view of yet another example of a grip area that is a modification of the grip area of the first arm in the same representation as in FIG. 5.

In the variations shown in FIGS. 6 and 7, the first grip area 6 can be designed as a so-called flat grip, so that there is no continuous curvature. The cross-sectional shape can be rectangular (FIG. 6) or trapezoidal (FIG. 7).

In order to further improve the feel of the first grip area 6, curved grooves 27 are formed on the outer side, which extend transversely to the longitudinal direction 19. The grooves 27 are spaced apart in the longitudinal direction 19, so that raised arcuate areas 28, which are raised or protrude relative to the grooves 27, are formed between the grooves 27. Each raised area 28 has a central flat section 29 and two lateral flat sections 30 and 31 spaced apart transversely to the longitudinal direction 19. The flat sections 29, 30 and 31 are connected by curved intermediate sections 32 and 33.

As can be seen from the illustration in FIG. 2, the third and fourth elongated holes 22, 23 extend through the middle flat sections 29 of the corresponding raised areas 28, so that the elongated holes 22, 23 and the middle flat sections 29 are on one level and the user can easily get in contact with the elongated holes 22, 23. The first and second elongated holes 20, 21 and the fifth and sixth elongated holes 24, 25 extend through the curved intermediate sections 32 and 33 respectively.

The described design of the first grip area 6 and the corresponding design of the second grip area 10 enables the user to hold and use the medical instrument 1 safely, e.g. between his thumb and index finger. Slipping in the longitudinal direction 19 is prevented in particular by the elongated holes 20 to 25. Since at least two elongated holes 20, 21; 22, 23; 24, 25 are arranged one behind the other in longitudinal direction 19, there are various optimum gripping positions for the user on the grip areas 6, 10. The user can preferably hold the grip areas 6, 10 at the ends of the elongated holes 20-25 facing the front ends 7, 11.

Figure 10:
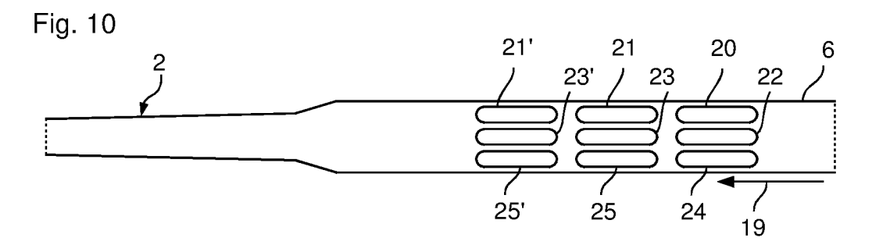
FIGS. 10-21 are schematic representations of a grip area of a first arm of medical instruments that are variations of the instrument of FIG. 1.
Figure 11:
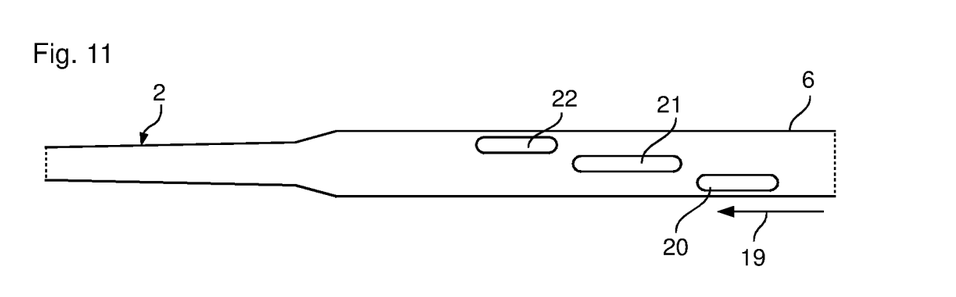

The formation of three pairs with two elongated holes 20-25 each per grip area 6, 10 is to be understood purely as an example. It is essential that at least two elongated holes 20, 21; 22, 23; 24, 25 are provided per grip area 6, 10, which are arranged offset to each other in the longitudinal direction 19 (here one behind the other). E.g., three or four elongated holes can thus also be provided one behind the other. The elongated holes arranged one behind the other can be arranged on a line as described above. Thus, as can be seen in the schematic diagram in FIG. 10, three groups of three elongated holes 20, 21, 21'; 22, 23, 23' and 24, 25 and 25' can be arranged one behind the other. In particular, the pairs or groups of elongated holes arranged one behind the other can be arranged parallel to each other. However, it is also possible that there is a lateral offset, as shown schematically in FIG. 11.

Figure 12:
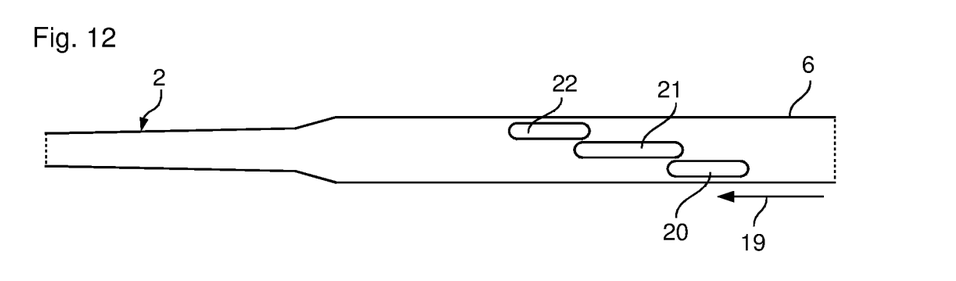

Furthermore, it is also not absolutely necessary that the at least two elongated holes 20, 21 are spaced from each other in the longitudinal direction, as was the case with the embodiments described so far. It is also possible that there is a partial overlap (but not a complete overlap) in the longitudinal direction 19, as shown for the elongated holes 20, 21 and 22 in FIG. 12. In addition, the elongated holes can be arranged offset to each other in the longitudinal direction 19 in such a way that the front and/or rear ends of two elongated holes are offset to each other in the longitudinal direction 19 or spaced apart from each other. This applies, for example, to the rear ends 20H and 21H of the two elongated holes 20 and 21 in the embodiment in FIG. 13. The front ends 20V and 21V of the two elongated holes are at the same height in longitudinal direction 19.

Figure 13:
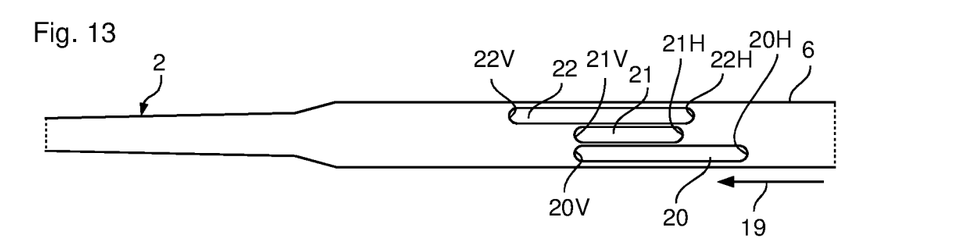

In case of the two elongated holes 21 and 22 according to FIG. 13, both the front ends 21V and 22V and the rear ends 21H and 22H are offset to each other in longitudinal direction 19, although the elongated hole 22 completely overlaps the elongated hole 21 in longitudinal direction 19. This is the case here because the two elongated holes 21 and 22 are of different lengths.

Figure 14:
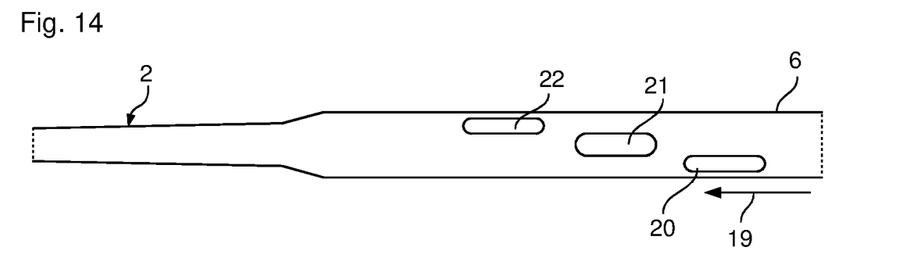
Figure 15:
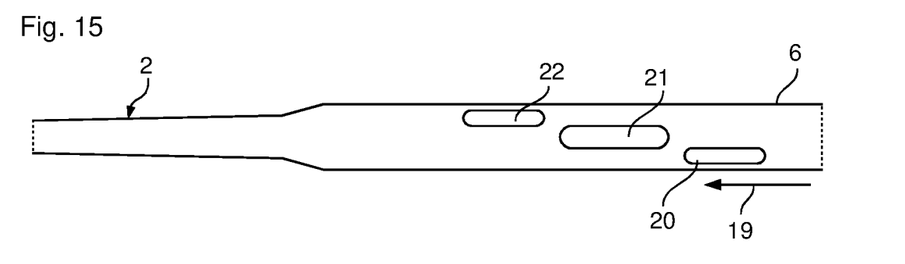

Of course, in the other embodiments described, the elongated holes 20-25 can also be of different lengths in the longitudinal direction 19 and/or of different widths (extension transverse to the longitudinal direction 19), as shown in FIGS. 14 and 15. In the embodiment of FIG. 14 the elongated hole 21 is wider than the other two elongated holes 20 and 22 and in the embodiment of FIG. 15 the elongated hole 21 is both wider and longer than the other two elongated holes 20 and 22.

Figure 16:
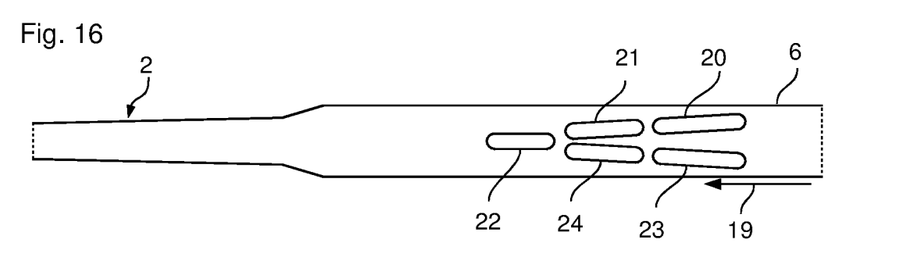

Of course, in the embodiments shown in FIGS. 14 and 15, it is also possible that the elongated hole 20 and/or 22 are/is wider than the elongated hole 21. In the embodiments described so far, the elongated holes 20-25 always extend parallel to the longitudinal direction 19. This is not absolutely necessary. As shown schematically in the design example in FIG. 16, the elongated holes 20 and 21 are arranged at a certain angle to the longitudinal direction 19. This angle can be in the range of 2°-7°, for example. The elongated holes 23 and 24 are then arranged at the corresponding negative angle. The arrangement of the elongated holes 20, 21 and 23, 24 can also be described as V-shaped. Furthermore, the elongated hole 22 is also arranged, which extends parallel to the longitudinal direction 19.

Figure 17:
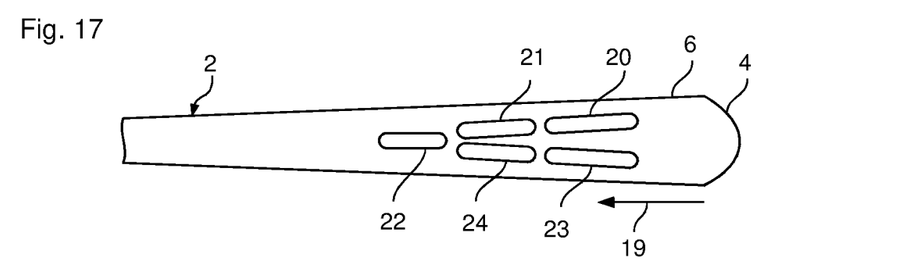

FIG. 17 shows the same arrangement of the elongated holes 20-24, but the grip area 6 is designed with a removable width in longitudinal direction 19.

Figure 18:
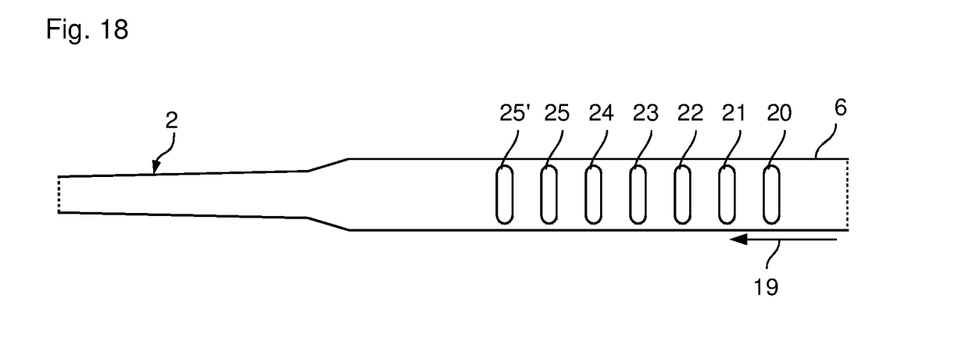

It is also possible that the elongated holes extend transversely to the longitudinal direction, as shown schematically in the embodiment in FIG. 18. In this case, the elongated holes extend 20-25, 25' perpendicular to the longitudinal direction 19, but any other angle from the range 0°-90° is also possible.

Figure 19:
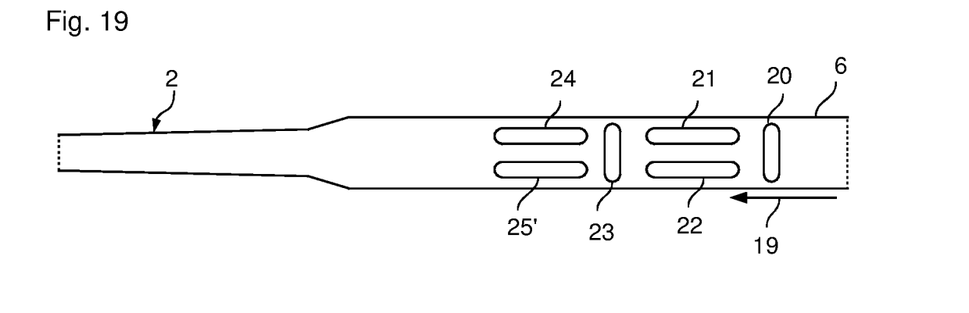

Furthermore, the elongated holes can also be arranged alternately perpendicular to the longitudinal direction 19 and parallel to the longitudinal direction 19, as shown schematically in FIG. 19.

Figure 20:
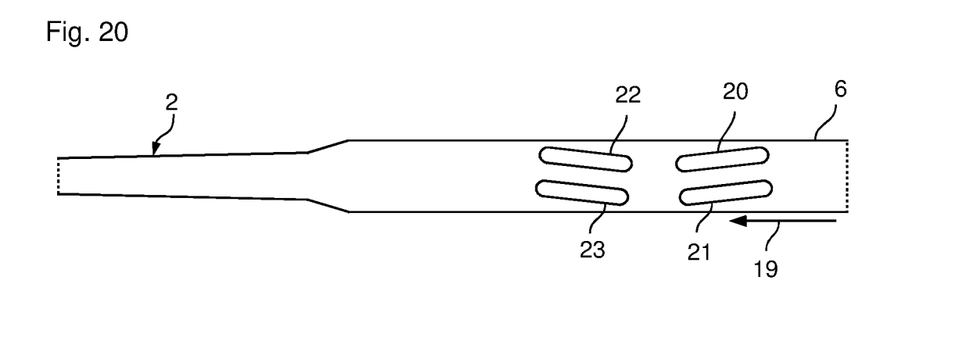

FIG. 20 shows different angles to the longitudinal direction 19 for the elongated holes 20, 21 and 22, 23.

Figure 21:
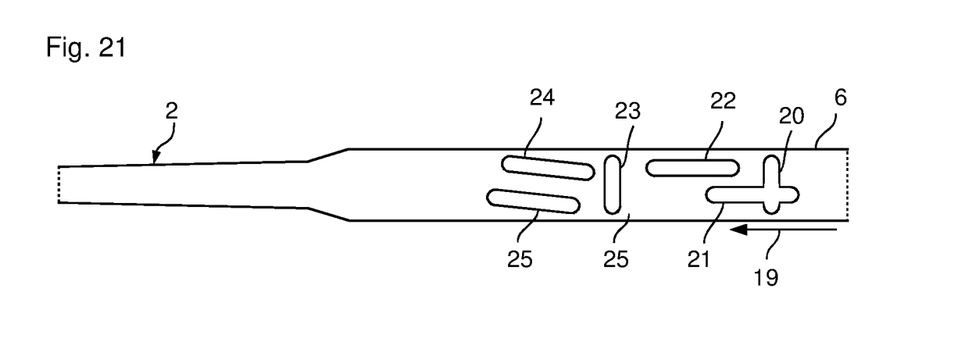

FIG. 21 shows an embodiment in which the elongated holes 20 and 21 cross or intersect. Furthermore, there are other elongated holes 22, 23, 24 and 25, which have different angles to the longitudinal direction 19.

The arrangement and formation of the elongated holes according to FIGS. 10-21 are to be understood purely as examples and it is possible to combine the variants or parts of them shown in these figures.

In the embodiments shown in FIGS. 10 to 21, the grooves 27 and raised areas 28 are not provided in comparison to the embodiment shown in FIGS. 1 to 5. However, it is optionally possible to form such grooves 27 and raised areas 28 in the variants according to FIGS. 10 to 21 in the same way as in the embodiment according to FIGS. 1 to 5.

Figure 22:
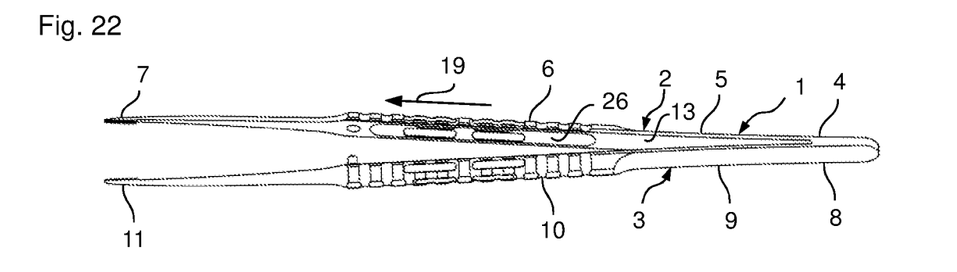
FIG. 22 is a perspective view of a second embodiment of the medical device according to the invention.

The medical instrument 1 can also be designed as tweezers, for example, as shown in FIG. 22. The tweezers as shown in FIG. 22 have elongated holes 20-25 in the first and second grip area 6, 10 of the first and second arm 2, 3 in the same way as the needle holder as shown in FIGS. 1-5. Only the connection of the rear ends 4, 8 and the design of the front ends 7, 11 are different to provide the desired functionality of a pair of tweezers. In this case the rear ends 4, 8 are firmly connected to each other.

Figure 23:
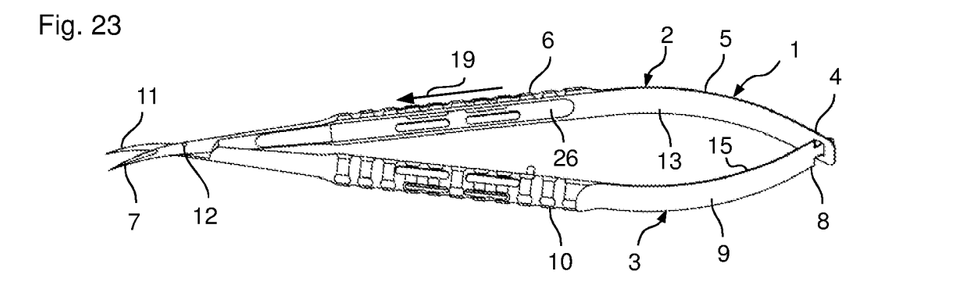
FIG. 23 is a perspective view of a third embodiment of the medical device according to the invention.

FIG. 23 shows a pair of scissors 1, which differs essentially from the needle holder 1 in FIG. 1 by the formation of the working ends 7, 11. Again, it is essential that the grip areas 6, 10 of the two arms 2, 3 are designed in the same way.

The medical instrument 1 can have an extension in longitudinal direction 19 for example in the range of 4 to 30 cm and in particular in the range of 10 to 25 cm or 15-20 cm. For example, the length can be 16.5 cm, 17.5 cm 18 cm or 20 cm. The maximum dimension of an arm 2, 3 transverse to the longitudinal direction 19 can be in the range of 5 to 30 mm and in particular in the range of 7 to 20 mm. For example, the width of the arm 2, 3 can be 7.5 mm, 10 mm or 18 mm.

The materials that can be used are in particular plastic, ceramics, metal, steel, stainless steel and/or titanium. Of course, known metal alloys can also be used.

In the embodiments described so far, the two grip areas 6 and 10 have the same design (especially with regard to the elongated holes 20-25). However, this is not absolutely necessary. Of course, the two grip areas 6 and 10 can be designed differently. This different design can particularly affect the elongated holes 20-25. For example, the number, arrangement and/or dimensions of the elongated holes 20-25 can be different for the two grip areas 6, 10.

In the embodiments described so far, the medical instrument 1 always has two arms 2, 3 (or two legs 2, 3). Of course, it is also possible that the medical instrument 1 has only one arm 2, as shown in the embodiment in FIG. 24. The front working end 7 has a spoon-like design and in the grip area 6 there are three elongated holes 20, 21 and 22 arranged offset to each other in the longitudinal direction 19. The elongated holes 20-21 are designed as through holes. In a variation they can also be designed as grooves 20-22 and thus as longitudinal grooves 20-22.

The grip area 6 can be hollow. However, it is also possible to have a non-hollow design so that the handle can be described as full.

Figure 24:
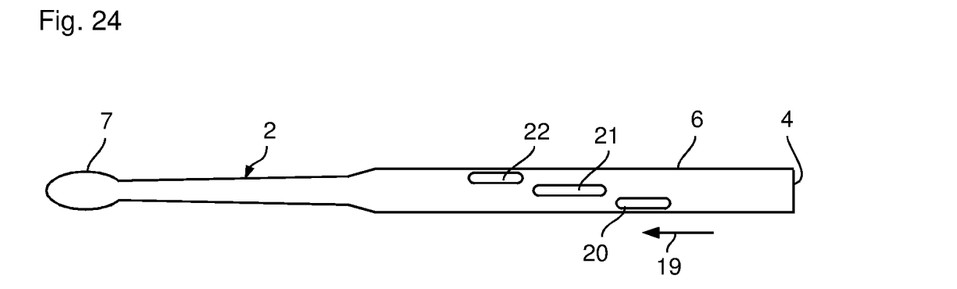
FIG. 24 is a perspective view of a fourth embodiment of the medical device according to the invention.

In the embodiment shown in FIG. 24, the medical instrument has a working end 7 and can therefore also be described as a single ended instrument 1. Of course, it is also possible to design the medical instrument 1 with only one arm 2 and two working ends 4, 7, as shown in FIG. 25.

The first end 4 can be described as the first working end 4 (here as curved tip 4) and the front end 7 can be described as the second working end 7, which is again spoon shaped. In this embodiment, the grip area 6 has three elongated holes 20, 21 and 22, which are offset to each other in the longitudinal direction 19.

Figure 25:
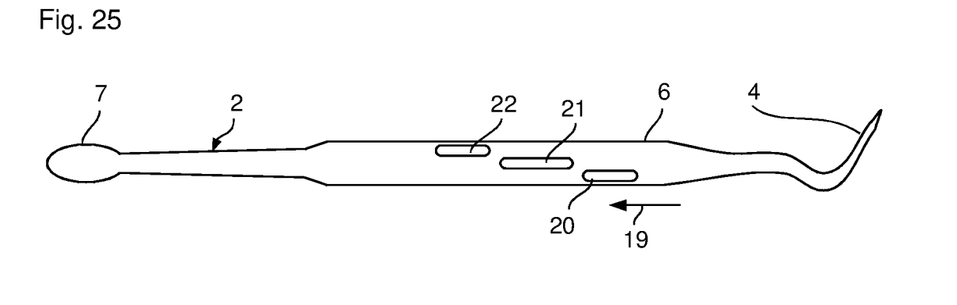
FIG. 25 is a perspective view of a fifth embodiment of the medical device according to the invention.

Of course, the grip areas 6 of the medical instruments 1 according to FIGS. 24 and 25 can also have all the arrangements of elongated holes 20-25 described in relation to FIGS. 1 to 23. In addition, the grip areas of medical instruments 1 as shown in FIGS. 24 and 25 can also have the structure of grooves 27 and raised areas 28 as described.

In the embodiments described so far, at least the grip areas 6, 10 are always straight. However, it is also possible that the grip areas 6, 10 have a curved course in the direction from the rear to the front end 4, 7.

In some examples, the medical instrument can be designed with a so-called finger grip or without a finger grip and therefore neutral. This applies to the single-arm and two-arm versions. If the arm is designed as a finger grip, a preformation for the fingers of the right hand is formed, so that a corresponding operation with the right hand is predetermined. The finger grip design is often offered to prevent slipping. In this case, however, the medical instrument, e.g. dental pliers, has to be operated with the right hand only. By providing the elongated holes, however, the design as a finger grip can be dispensed with, as the elongated holes can safely prevent slipping. This means that the medical instrument (e.g. the dental pliers) can be used safely by both right-handed and left-handed people. Furthermore, the reprocessing of the medical instrument is easily possible.

The invention claimed is:

1. A medical instrument comprising:
a first arm extending in a longitudinal direction and having a grip area between a rear end and a front working end,
the first arm comprising an inner recess formed on a first inner side, the inner recess extending beyond the grip area in the longitudinal direction,
wherein at least two groups of at least two elongated holes are formed in the grip area and are arranged offset to each other in the longitudinal direction,
wherein the at least two groups of at least two elongated holes are arranged offset to each other transversely to the longitudinal direction,
wherein at least one of the elongated holes is designed as a through hole,
wherein at least two of the elongated holes have a length extending in the longitudinal direction and a width extending in a transverse direction, the length being longer than the width,
wherein the at least two elongated holes of each group are on a straight line,
wherein the at least two groups of at least two elongated holes overlap in a lateral direction; and
wherein a plurality of grooves are formed in the grip area spaced apart from one another in the longitudinal direction, each one of the plurality of grooves running transversely to the longitudinal direction so that a raised area is present between adjacent ones of the plurality of grooves, and the raised area comprises an arcuate section and a plurality of flat sections, the respective ones of the plurality of flat sections being spaced apart transversely to the longitudinal direction.

2. The medical instrument of claim 1, wherein at least one of the elongated holes comprises two ends of the elongated hole that are rounded.

3. The medical instrument of claim 1, wherein two of the elongated holes differ in their extension in the longitudinal direction.

4. The medical instrument of claim 3, wherein the groups of at least two elongated holes run parallel to each other or enclose an angle with each other which is in the range of greater than 0° and less than or equal to 20°.

5. The medical instrument of claim 1, wherein the plurality of flat sections comprises a central flat section and two lateral flat sections, and wherein the arcuate section comprises a first curved intermediate section and a second curved intermediate section, the first curved intermediate section disposed between the central flat section and a first one of the two lateral flat sections and the second curved intermediate section disposed between the central flat section and a second one of the two lateral flat sections.

6. The medical instrument of claim 1, wherein the grip area is curved in an area of the elongated holes.

7. The medical instrument of claim 1, wherein at least one of the elongated holes has two sides running parallel to each other.

8. The medical instrument of claim 1, further comprising a second arm extending in the longitudinal direction and having a grip area between a rear end and a front working end,
wherein the first and second arms are connected to each other at their rear ends and/or their front working ends, and
wherein at least two elongated holes extending in the longitudinal direction are formed in the grip area of the second arm and are arranged offset to one another in the longitudinal direction of the second arm.

9. The medical instrument of claim 8, wherein a first element is attached to the first inner side of the first arm and a corresponding second element is attached to a second inner side of the second arm, and
wherein the first element and the second element are engageable with each other so that the medical instrument is held in a holding position.

10. The medical instrument of claim 1, wherein the inner recess extends continuously beyond the grip area in the longitudinal direction toward the front working end.

11. The medical instrument of claim 10, wherein the first arm comprises a first cross sectional shape of a circular segment such that the first inner side is continuously curved in the grip area and interrupted only by the at least two groups of at least two elongated holes.

12. A medical instrument comprising:
a first arm extending in a longitudinal direction and having a first grip area between a rear end and a front working end, the first arm comprising a first inner recess formed on a first inner side, the first inner recess extending beyond the first grip area in the longitudinal direction; and
a second arm extending in the longitudinal direction and having a second grip area between a rear end and a front working end, the second arm comprising a second inner recess formed on a second inner side, the second inner recess extending beyond the second grip area in the longitudinal direction,
wherein the first and second arms are connected to each other at their rear ends and/or their front working ends, wherein at least two groups of at least two elongated holes are formed in at least one of the grip areas, which are arranged offset to each other in the longitudinal direction and offset to each other transversely to the respective longitudinal direction;

wherein at least two of the elongated holes have a length extending in the longitudinal direction and a width extending in a transverse direction, the length being longer than the width, wherein the at least two elongated holes of each group are on a straight line, wherein the at least two groups of at least two elongated holes overlap in a lateral direction; and wherein a plurality of grooves are formed in the grip areas, the plurality of grooves of each grip area spaced apart from one another in the longitudinal direction, each one of the plurality of grooves running transversely to the longitudinal direction so that a raised area is present between adjacent ones of the plurality of grooves, and the raised area comprises an arcuate section and a plurality of flat sections, the respective ones of the plurality of flat sections being spaced apart transversely to the longitudinal direction.

13. The medical instrument of claim 12, wherein the groups of at least two elongated holes run parallel to each other or enclose an angle with each other which is in the range of greater than 0° and less than or equal to 20°.

14. The medical instrument of claim 12, wherein the first arm comprises a first cross-sectional shape of a first circular segment and wherein the second arm comprises a second cross-sectional shape of a second circular segment.

15. The medical instrument of claim 14, wherein the grip area of the first arm is bent outwards away from the second arm and the grip area of the second arm is bent outwards away from the first arm.

16. The medical instrument of claim 12, wherein the first inner side is continuously curved in the grip area of the first arm; wherein the second inner side is continuously curved in the grip area of the second arm; wherein the first inner recess extends continuously beyond the grip area of the first arm in the longitudinal direction toward the front working end; and wherein the second inner recess extends continuously beyond the grip area of the second arm in the longitudinal direction toward the front working end.

* * * * *